United States Patent [19]

Sage et al.

[11] Patent Number: 4,911,863
[45] Date of Patent: Mar. 27, 1990

[54] ALKYLBYPHENYLOXYACETIC ACID ESTERS AND THEIR USE IN SMECTIC LIQUID CRYSTAL MATERIALS

[75] Inventors: Ian C. Sage; John A. Jenner, both of Poole, England; Hans A. Kurmeier, Seeheim-Jugenheim, Fed. Rep. of Germany; Pauluth Detlef, Darmstadt, Fed. Rep. of Germany; Claus Escher, Nieder-Remstadt, Fed. Rep. of Germany; Eike Poetsch, Mühltal, Fed. Rep. of Germany

[73] Assignee: The Secretary of State for Defence in Her Britannic Majesty's Government of the United Kingdom of Great Britain and Northern Ireland, London, United Kingdom

[21] Appl. No.: 117,065

[22] PCT Filed: Feb. 22, 1987

[86] PCT No.: PCT GB87/00131
§ 371 Date: Dec. 21, 1987
§ 102(e) Date: Dec. 21, 1987

[87] PCT Pub. No.: WO87/05012
PCT Pub. Date: Aug. 27, 1987

[30] Foreign Application Priority Data

Feb. 21, 1986 [GB] United Kingdom ............... 8604330
Feb. 26, 1986 [GB] United Kingdom ............... 8604739

[51] Int. Cl.⁴ ................. C09K 19/12; C09K 19/34; C09K 19/30; G02F 1/13

[52] U.S. Cl. .............. 252/299.65; 252/299.01; 252/299.66; 252/299.61; 252/299.63; 252/299.64; 252/299.67; 252/299.68; 350/350 S; 560/59; 560/61; 560/116; 560/8; 560/1; 560/106; 560/141; 544/298; 544/335; 546/301; 546/342

[58] Field of Search ........... 252/299.01, 299.61, 252/299.63, 299.64, 299.65, 299.66, 299.67, 299.68; 350/350 S

[56] References Cited

U.S. PATENT DOCUMENTS

| | | | |
|---|---|---|---|
| 3,652,646 | 3/1972 | Leigh et al. | 560/59 |
| 3,755,603 | 8/1973 | Harison et al. | 560/59 |
| 4,556,727 | 12/1985 | Walba | 252/299.67 |
| 4,576,732 | 3/1986 | Isogai et al. | 252/299.65 |
| 4,596,667 | 6/1986 | Inukai et al. | 252/299.65 |
| 4,614,609 | 9/1986 | Inoue et al. | 252/299.66 |
| 4,725,688 | 2/1988 | Taguchi et al. | 252/299.01 |
| 4,753,752 | 6/1988 | Raynes et al. | 252/299.65 |
| 4,764,619 | 8/1988 | Gunjima et al. | 252/299.61 |
| 4,775,223 | 10/1988 | Yoshinaga et al. | 252/299.01 |
| 4,780,241 | 10/1988 | Farukawa et al. | 252/299.63 |

FOREIGN PATENT DOCUMENTS

| | | |
|---|---|---|
| 3515373 | 11/1986 | Fed. Rep. of Germany ............... 252/299.61 |
| 3515374 | 11/1986 | Fed. Rep. of Germany ............... 252/299.61 |
| 3638119 | 5/1988 | Fed. Rep. of Germany . |
| 87/07890 | 12/1986 | World Int. Prop. O. . |
| 87/05017 | 8/1987 | World Int. Prop. O. . |
| 87/05018 | 8/1987 | World Int. Prop. O. ...... 252/299.61 |

Primary Examiner—John F. Terapane
Assistant Examiner—J. E. Thomas
Attorney, Agent, or Firm—Stevens, Davis, Miller & Mosher

[57] ABSTRACT

The invention relates to ferroelectric smectic liquid crystal mixtures and compounds. The invention also relates to electro-optical devices incorporating these mixtures.

7 Claims, 1 Drawing Sheet

ROUTE A

ALKYLBYPHENYLOXYACETIC ACID ESTERS AND THEIR USE IN SMECTIC LIQUID CRYSTAL MATERIALS

FIELD OF THE INVENTION

This invention relates to liquid crystal mixtures and to compounds for use in them. The invention is particularly concerned with ferroelectric smectic liquid crystal mixtures and compounds. The invention also relates to electro-optical devices incorporating these mixtures.

DESCRIPTION OF THE INVENTION

Ferroelectric smectic liquid crystal materials utilize the ferroelectric properties of the chiral titlted smectic phase, ie the chiral smectic C, F, G, H, I, F and K phases (hereinafter designated $S_c^*$ etc, the asterisk * denoting chirality). The $S_c^*$ phase is most commonly sought for use in electro-optical devices as it is the most fluid, and it is also desirable that the material shows an $S_A$ phase at a temperature above the $S_c^*$ phase, to assist in surface alignment.

Ferroelectric liquid crystal materials ideally have a low viscosity, a broad smectic liquid crystal temperature range, stability ect., and in particular should show a high spontaneous polarisation co-efficient (Ps, measured in $nCcm^{-2}$). Although some single component materials show these properties, it has become common practice to use a mixture which shows a smectic phase. At least one of the compounds in the mixture is optically active (chiral) so as to induce the smectic phase shown by the mixture to be chiral, especially $S_C^*$. Such optically active compounds are called "chiral dopants".

According to the present invention a novel compound suitable for inclusion in a ferroelectric smectic liquid crystal mixture has a formula I:

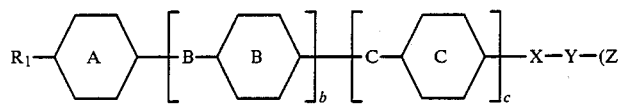

where $R_1$ and $R_2$ are independently selected from H, R, RO, ROOC, RCOO, RCOOCH(CH$_3$)COO and COOCH(CH$_3$)COOR where R is $C_{1-12}$ alkyl, or from CN or halogen;

where each of

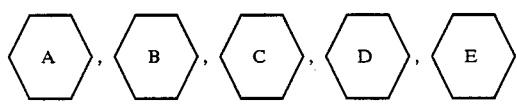

is independently selected from:

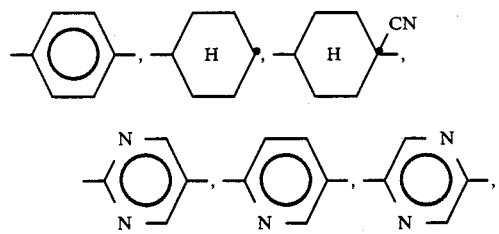

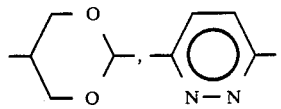

and these rings may carry one or more lateral substituents selected from halogen, CN or CH$_3$;

where B, C and D are independently selected from COO, OOC, CH$_2$CH$_2$, OCH$_2$, CH$_2$O, CH=N, N=CH, N=N or a single bond;

where each of b, c, d, e and z is independently 0 or 1, provided (b+c+d+e) is 1, 2 or 3;

where each of X, Y, Z are different and are selected from —O—, COO, OOC, CH$_2$ or

where W is $C_{1-5}$ alkyl, phenyl, cyclohexyl, halogen or CN, provided that when W is CN then d or e is 1, and further provided that rings

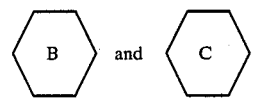

when present have the same lateral substitution pattern.

Compounds of formula I are useful constituents of ferroelectric smectic liquid crystal mixtures. According to a second aspect of the invention there is provided a ferroelectric smectic liquid crystal mixture containing at least two compounds, at least one of which is a compound of formula I.

Suitability for use in such a mixture is among the factors determining the structural and other preferences discussed below.

The compound of formula I may be optically active, racemic, or non-optically active, but the mixture preferably contains at least one optically active compound of formula I.

The alkyl group R may be straight chain (—n), branched or when present in other than RCOOCH(CH$_3$)COO or COOCH(CH$_3$)COOR may be chiral. Preferably $R_1$ and $R_2$ are independently alkyl, alkoxy, alkanoyloxy or alkoxycarbonyl.

Preferred substituents when present of the rings

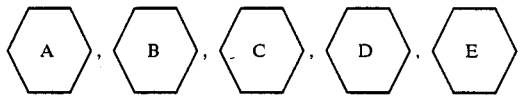

are F. Compounds wherein one of these rings is

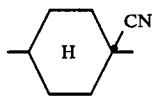

are pariculary useful.

Preferably W in formula I is n-alkyl, especially methyl.

Preferred structures for the unit —X—Y—(Z)—$_z$ in formula I are listed in table 1 below:

TABLE 1

| | |
|---|---|
| —O—CH(CH₃)—COO— | 1.1 |
| —OOC—CH(CH₃)—O— | 1.2 |
| —CH₂—CH(CH₃)—COO— | 1.3 |
| —COO—CH(CH₃)—CH₂— | 1.4 |
| —CH(CH₃)—CH₂— | 1.5 |
| —CH(CH₃)—COO—CH₂— | 1.6 |
| —CH(CH₃)—CH₂—COO— | 1.7 |
| —CH₂—COO—CH(CH₃)— | 1.8 |
| —CH(CH₃)—CH₂—OOC— | 1.9 |
| —CH₂—CH(CH₃)— | 1.10 |
| —O—CH₂—COO— | 1.11 |

Preferred structures for the unit

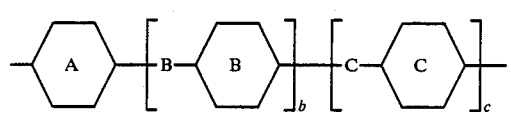

in formula I are listed in table 2 below:

TABLE 2 where the phenyl rings in the structures shown in table 2 may carry one lateral halogen substituent.

Preferred overall structures for the compound of formula I are listed in table 3 below:

TABLE 3

TABLE 3-continued

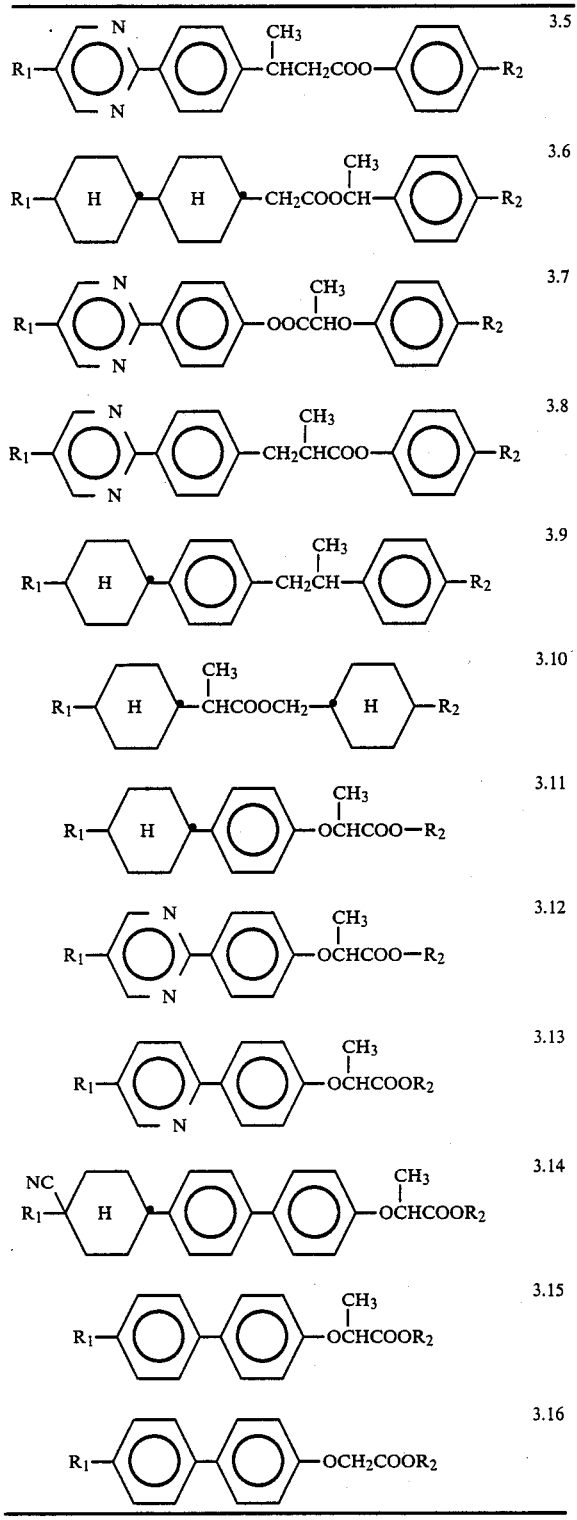

In table 3 $R_1$ is $C_{3-10}$ straight chain or branched alkyl or alkoxy, $R_2$ is $C_{1-12}$ alkyl or alkoxy, or if $R_2$ is bonded directly to a phenyl or cyclohexyl ring $R_2$ may also be alkanoyloxy, alkoxycarbonyl, $COOCH(CH_3)C_3H_7$ or $COOCH(CH_3)COOC_2H_5$. The phenyl rings in table 3 may carry one lateral halogen substituent.

Particularly preferred compounds shown in table 3 are those of structures 3.1, 3.2, 3.3, 3.4, 3.5, 3.6, 3.7, 3.8, 3.9, and 3.10 in which $R_2$ is 2-octyloxy (1-methylheptyloxy), and 3.16.

In structure 3.16 $R_2$ is preferably 2-methyl heptyl.

Preferably in formula I, R is $C_3$ to $C_{12}$ n-alkyl.

Japanese patent application No. 56925/1984 (laid open No. 199856/1985 discloses a series of exclusively racemic compounds related to formula I. That disclosure refers exclusively to their use in nematic liquid crystal mixtures. It is well known that the physics and chemistry of ferroelectric smectic liquid crystal mixtures is very different to that of nematic mixtures, particularly in terms of the requirement for miscibility and optical purity. Understanding of nematic systems thus provides very little guidance in formulating the far more idiosyncratic smectic mixtures.

A ferroelectric smectic liquid crystal mixture of the invention will normally consist of a number of compounds, and will include one or more optically active compounds, preferably at least one of which is a compound of formula I. The other compounds in the mixture will normally include at least one compound which either alone or mixed with some or all of the other compounds in the mixture shows a smectic phase, preferably $S_C$, and at least one of these compounds may be a compound of formula I in a racemic form. These other compounds are often called 'smectic hosts'

Some examples of smectic hosts include:

(a) The compounds, and mixtures thereof, disclosed in PCT/GB86/0040, eg of formula:

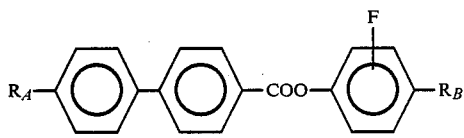

where $R_A$ and $R_B$ are independently selected from alkyl (preferably n-alkyl), alkoxy (preferably n-alkoxy), alkanoyloxy or alkoxycarbonyl (preferably n-alkoxycarbonyl) and contain 1–12 carbon atoms, preferably 3 to 10 carbon atoms. Preferred compounds of this type have structures:

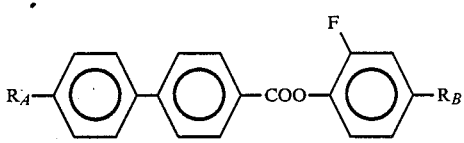

or

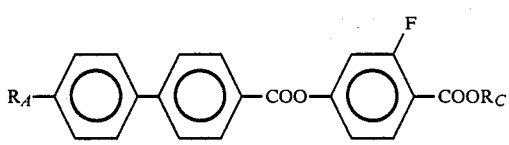

where $R_C$ is alkyl.

(b) The compounds, and mixtures thereof, of formula:

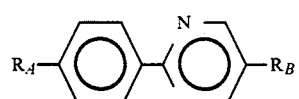

where $R_A$ and $R_B$ are independently alkyl (preferably n-alkyl) or alkoxy (preferably n-alkoxy) and contain up to 12 carbon atoms.

(c) Other examples of known smectic host compounds include those of the following general formulae:

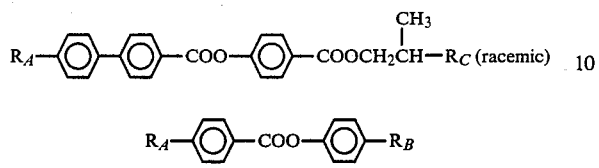

where $R_A$ and $R_B$ are independently selected from n-alkyl and n-alkoxy and $R_C$ is n-alkyl, preferably ethyl.

(d) r-1-cyano cis-4-(4'-alkyl or alkoxy-biphenyl-4-yl)-1-alkyl or alkoxy cyclohexanes;

r-1-cyano cis-4-(trans-4-alkyl or alkoxy cyclohexyl)-1-(trans-4-alkyl or alkoxy cyclohexyl)-cyclohexanes.

The mixture may also contain other optically active compounds which are miscible with smectic materials, for example the lactic acid derivatives disclosed in PCT GB/85/00512, eg

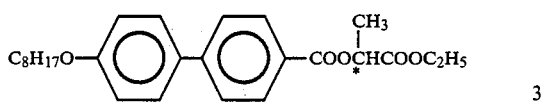

or the compounds disclosed in European Pat. No. 0,110,299, eg:

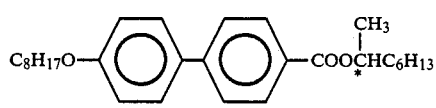

or the terpenoid derivatives disclosed in PCT/GB86/0046.

If the mixture includes more than one optically active compound, eg a compound of formula I and one of the other optically active compounds mentioned above, then the helical twist senses of the S* phase induced by these compounds may be the same or opposite, eg. by the use of both (+) and (−) optically active compounds. It is often desirable to include compounds which induce opposite twist senses of the S* phase in order to increase the helical pitch length. It is desirable that each optically active compound in the mixture induces the same sense of Ps in the mixture.

The mixture may also contain other known additives to improve the properties, eg Ps. Sc phase breadth, viscosity etc. or to induce the appearance of an $S_A$ phase of a temperature above the $S_C^*$ to assist alignment. An example of a class of compounds which may be used to broaden the Sc phase is:

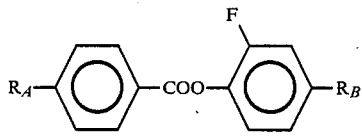

where $R_A$ and $R_B$ are independently $C_{1-12}$ n-alkyl or n-alkoxy.

The mixture may also contain pleochroic dyes.

Typically but not exclusively a ferroelectric smectic liquid crystal mixture of the invention will have the following composition:

| | |
|---|---|
| One or more smectic host compounds | 30–99 weight % |
| Optically active compound(s) of formula 1 | 1–50 weight % |
| Other optically active compound(s) | 0–20 weight % |
| Additives and pleochroic dye if present | 0–20 weight % |
| Racemic compounds(s) of formula I | 0–20 weight % |

The total being 100 weight %. The nature and relative proportions of the various components of a liquid crystal material of the invention will depend upon the use for which the material is intended, and some experimentation may be necessary to suit a particular requirement, but the basic principles of mixing and assessment of such materials is well known in the field.

Compounds of formula I may be prepared by generally applicable routes. Those which are esters, ie. contain a —COO— or —OOC— group may be prepared by any of the well known methods of ester synthesis to form the novel products. Some examples of general routes are shown in the experimental examples which follow. A general route for compounds which contain the group $$-O-CH(CH_3)-COO- \text{ or } -OOC-CH(CH_3)-O-$$

is Route A shown in FIG. 1, where:
(i) $K_2CO_3$, butanone
(ii) KOH, IMS, $H_2O$
(iii) $SOCl_2$
(iv) $(C_2H_5)_3N$, $CH_2Cl_2$,

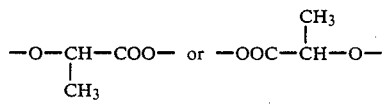

R, $R_2$ are alkyl or alkoxy.

The sulphonate used in step A(i) is a sulphonate of commercially available ethyl lactate.

In route A the product of each step should be checked for optical activity if an optically active compound of formula I is required.

Methods of preparation of other compounds of formula I will be apparent to the skilled chemist from the experimental examples.

The liquid crystal materials of the invention may be used in any of the known types of ferroelectric smectic liquid crystal display device, eg. the "Clark-Lagerwall Device" described in Appl. Phys Lett (1980), 36 899 and in Recent Developments in Condensed Matter Physics (1981), 4,309. The physics of this type of device and the method of constructing it are well known, and are described for example in PCT/GB85/00512, and PCT/GB86/0040. In practice such a device usually consists of two substrates, at least one of which is optically transparent, electrodes on the inner surfaces of the substrates by which a voltage may be applied and a layer of the liquid crystal materials sandwiched between the substrates. It is desirable that the helical pitch length of the $S_C^*$ phase is comparable to the thickness of the material, which is why long pitch mixtures are useful. The materials of the invention may be used in both the birefringence type display mode and the guest-host type display mode of the Clark-Lagerwall device/ The device may for example be in the form of a clock, calculator or video screen display, and methods of making the device in this form will be well known to those skilled in the art.

BRIEF DESCRIPTION OF THE DRAWINGS

The invention will now be described by way of example only, with reference to.

EXAMPLES

Figure 1:
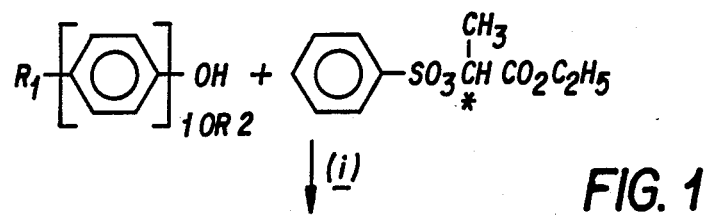
FIG. 1 which shows preparative route A.
Figure 1:
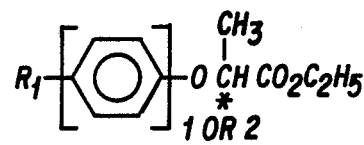
Figure 1:
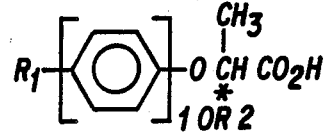
Figure 1:
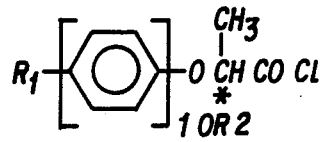
Figure 1:
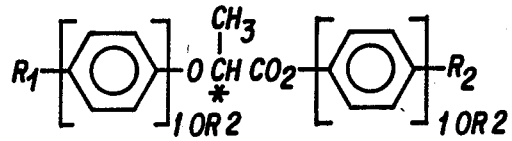

Note: Throughout this description and the following examples,

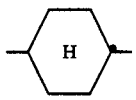

represents trans- cyclohexyl. The following examples illustrate the invention but do not limit it.

EXAMPLE 1.

Preparation of
(4-n-Pentyl-4'-biphenylyl)-2-(4''-octoxyphenyloxy)-(S)-propionate (Route A)

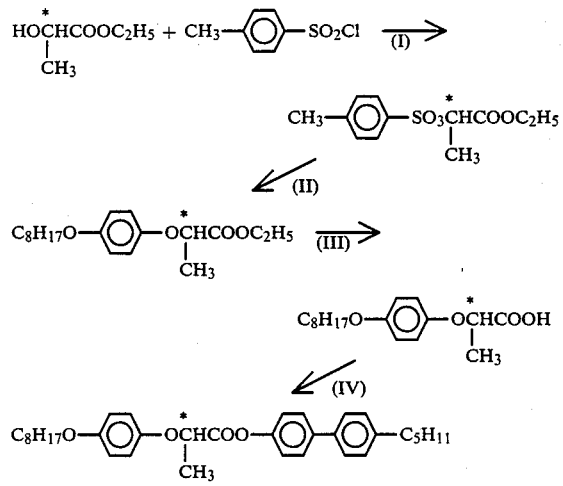

Stage I, Ethyl-2(4'-toluene sulphonyloxy) (S)-propionate

Ethyl L-(+)-lactate (25 gram. 0.2119 moles) was stirred at room temperature with toluene-4-sulphonyl chloride (50.5 gram, 0.2648) moles and pyridine (75 mls). After 3 hours water (3 mls, 0.1667 moles) was added and the stirring was continued for a further 1 hours. The organic layer was separated and the aqueous layer extracted with dichloromethane (2×150 mls). The combined organic material was washed with water (200 mls) and the solvent distilled off using a steam bath. Stage 1 product, 50.9 gram, 88% yield was obtained which was purified by recrystallisation from propan-2-ol (150 mls) to produce 30.9 gram of a white solid melting at 32°–33° C., and having a purity by HPLC of 99.9%.

Stage II, Ethyl-2-(4'-n-octoxyphenyloxy) (S)-propionate (step A(i))

Stage I product (10 gram, 0.03676 moles) was stirred and boiled under reflux with 4-n-octoxyphenol (8.16 gram, 0.03676 moles) and anhydrous potassium carbonate (10 gram) in butanone (100 mls) for 24 hours. The product isolated by addition of the cooled reaction mixture to water (200 mls) followed by separation and extraction of the aqueous with dichloromethane (2×150 mls). The combined organic material was washed with water (200 mls) then dried over sodium sulphate and evaporated to dryness to give a crude yield of 18.25 g. This was purified by column chromatography on basic aluminal (72 g) and eluted with petroleum spirit (bp 60°-80°). This gave a yield of 10.0 g, 85%.

Stage III, 2-(4'-Octoxyphenyloxy) (S)-propionic acid (step A(ii))

Stage II (11.9 gram, 0.03696 moles) was boiled under reflux with potassium hydroxide (6 g) industrial methylated spirit (75 mls) and water (15 mls) for 3¼ hours. The product was isolated by adding the cooled reaction mixture to 10% hydrochloric acid (250 mls). The product was filtered off, washed with water and dried in vacuum at 40° C. A yield of 8.9 g, 82% was obtained.

Stage IV, (4-n-Pentyl 4'-biphenylyl) 2-(4''-octoxyphenyloxy)-(S)-proprionate (steps A(iii) and (iv))

The above was prepared by first forming the acid chloride of stage III. Stage III (8.5 g, 0.02891 moles) was boiled under reflux with thionyl chloride (27 mls) for 2 hours, the excess thionyl chloride was then evaporated off on a steam bath and finally under high vacuum (0.1 mbar). This acid chloride was then added to 4'-hydroxy-4-n-pentyl biphenyl (6.9 g, 0.02891 moles) dissolved in dichloromethane (125 mls) and triethylamine (12.5 mls). This mixture was boiled under reflux for 1 hour and 10 minutes, allowed to cool and the product isolated by addition to water, (150 mls) followed by separation and subsequent washing with hydrochloric acid (150 mls of 10%) and with water (150 mls). The solvent was evaporated off to give a yield of crude product, 13.6 g, 91.3% of theory. This was purified by column chromatography on basic alumina (50 g) and eluted with petroleum spirit (bp 60°-80°) and dichloromethane mixture in the ratio 2:1. A yield of 9.0 grams, 60.4% of theory was obtained which was further purified by recrystallisation from industrial methylated spirit (70 mls) plus pyridine (0.75 mls). (4-n-Pentyl-4'-biphenylyl) 2-(4''-octoxyphenyloxy)-(S)-propionate (8.0 gram) was obtained in a yield of 54% of theory, and having a melting point, K-I of 86° C.

The spontaneous polarisation Ps of the product of Example 1 was measured at 10 wt % concentration in a mixture of:

33.3% 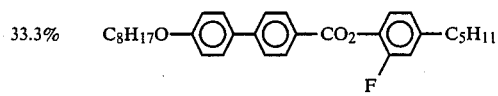

33.3% 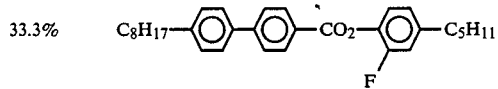

33.3% 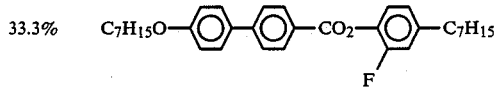

which had the transition temperature $S_c$-$S_A$ 90°, $S_A$-Ch 94° and Ch-I 133°–136°.

The variation of spontaneous polarization of this mixture with temperature was as follows:

| T(°C.) | $P_3(nC/cm^2)$ |
|---|---|
| 50 | 0.41 |
| 55 | 0.59 |
| 60 | 0.75 |
| 70 | 0.87 |
| 80 | 0.80 |
| 85 | 0.56 |
| 88 | 0.28 |
| 89 | 0.16 |

By an analogous method the compound:

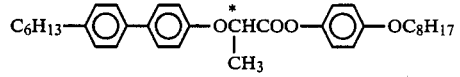

was prepared, having a melting point crystal - isotropic of 84° C.

EXAMPLE 2

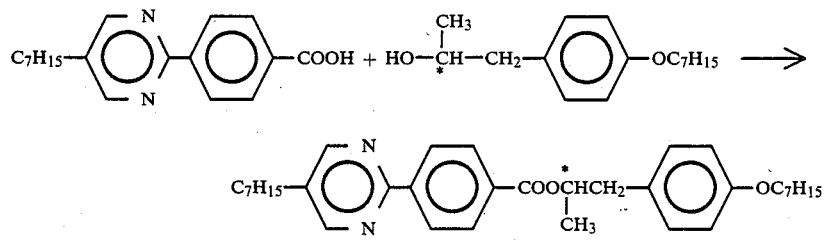

2.98 g (0.01 mole) of 4-(5-heptylpyrimidinyl-(2))-benzoic acid, 2.5 g (0.01 mole) of levorotatory 3-(4-heptyloxy phenyl-(1))-propanol-(2), $\alpha_D^{20} = -3.15$ (c=1 in $CH_2Cl_2$), prepared from commercially available R-propylenoxide and heptyloxyphenylmagnesiumbromide, 2,3 g of dicyclohexylcarbodiimide, 0.2 g of 4-N,N-dimethylaminopyridine and 25 ml of dichloromethane are stirred together 48 hours at room temperature. Thereafter, the reaction mixture is cooled down by external ice and the precipitate of dicyclohexylurea is filtered off and washed with dichloromethane. The combined filtrates of the dichloromethane solutions are chromatographied after evaporation on silica gel with toluene/2% ethylacetate. The main fraction yields after crystallisation from ethanol 1-(p-heptyloxyphenyl)-2-propyl-4-(5-heptylpyrimidinyl-(2))-benzoate, which is according to HPLC 99.1% pure.

($\alpha_D^{20} = -80.6$); M.Pt 76.2° C. melting enthalpy 8.16 kcal/mole$^{-1}$.

In a similar way the following acids yield the corresponding esters by esterification with levorotatory 1-(4-heptyloxyphenyl)-2-propanol:

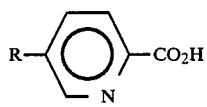

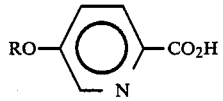

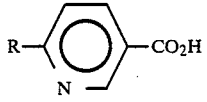

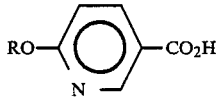

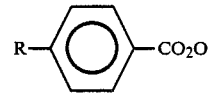

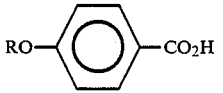

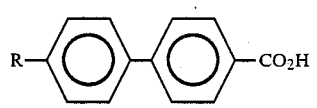

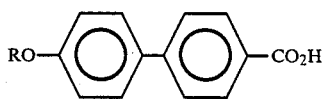

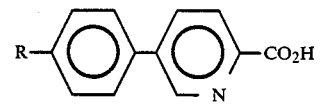

-continued

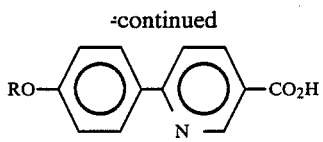
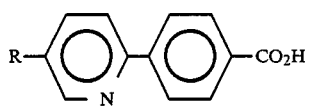
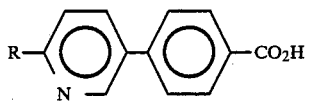
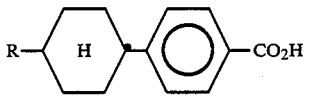
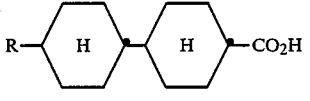
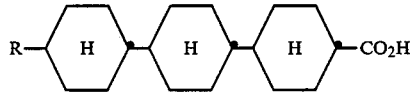
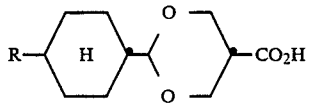
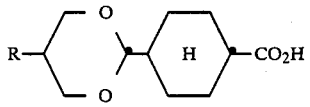
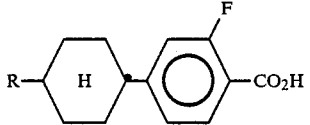

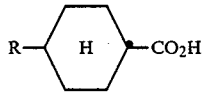
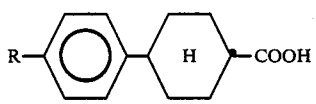

EXAMPLE 3

Esterification of optically active 1-(4'-heptyloxybiphenyl-4-yl)-propane-2-ol (prepared from R-propylenoxide and 4'-heptyloxybiphenyl-4-yl-magnesiumbomide) with butyric acid in a similar way as described in example 2 yields optically active 1-(4'-heptyloxybiphenyl-4-yl)-2-propyl butyrate. In a similar way the following 2-propanol derivatives yield the corresponding esters by sterification with aliphatic carboxylic acids:

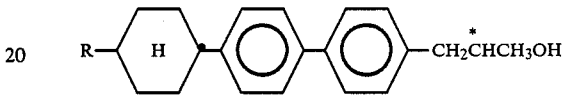
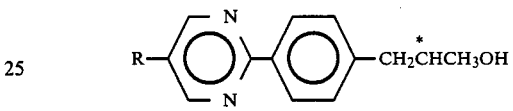
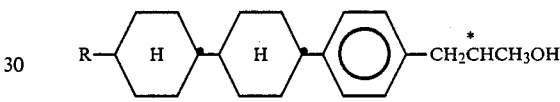
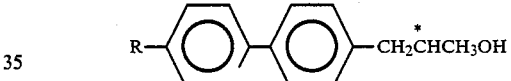
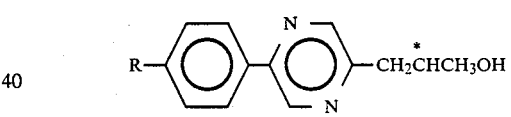
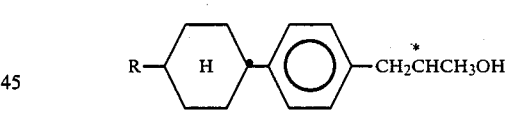

EXAMPLE 4

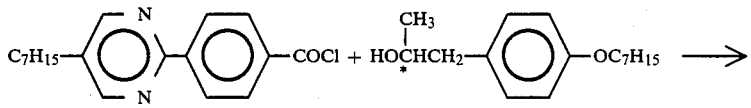
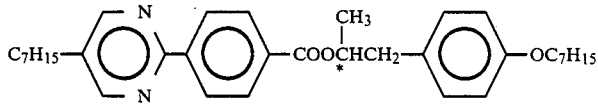

3.16 g (0.01 mole) of 4-(5-heptyloxypyrimidinyl-(2))-benzoic acid chloride are added to 15 ml of pyridine containing 2.5 g (0.01 mole) of dextrorotatory 3-(4-heptyloxyphenyl-(1))-propanol-(2), $\alpha_D^{20} = +3.14$ (c=1 in $CH_2Cl_2$), prepared from commercially available S-propylenoxide and heptyloxyphenylmagnesium bromide, at 0° C. under stirring. After completed addition the reaction mixture allowed to warm up to room temperature and stirred overnight. The mixture is then poured into 150 ml of water and extracted with toluene. The toluene layer is subsequently washed with diluted HCl, diluted NaOH and water, then dried over $Na_2SO_2$ and evaporated. The residue is chromatographied over silica gel by eluting with toluene yielding the ester, which after crystallization from acetonitrile and cyclohexane give pure material of 1-(p-heptyloxyphenyl)-2-propyl-4-(5-heptylpyrimidinyl-(2))-benzoate.

$\alpha_D^{20} = +79.6$; M.Pt 76.2° C.

Analogously the corresponding esters were prepared by esterification of the following acid chlorides with dextrorotatory 3-(4-heptyloxyphenyl-(1))-propanol-(2)

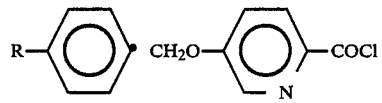

EXAMPLE 5

3.4 g (0.01 mole) of dextrorotatory 3-[4-(5-heptylpyrimidinyl-(2))-phenyl-(1)]-butyric acid, prepared by hydrogenation of the corresponding 2-butenic acid on 5% Pd/charcoal in tetrahydrofuran and resolution by (+)ephedrin (2-methylamino-1-phenylpropanol-(1)), $\alpha_D^{20} = +3.30$ (c=1 in $CH_2Cl_2$), are esterified by the method given in example 1 with 1.42 g of trans 4-propylcyclohexanol. After purification by chromatography and crystallization optically active trans-4-propylcyclohexyl-3-[4-(5-heptylpyrimidinyl-(2))-phenyl-(1)]-butyrate is obtained.

Analogously by esterification with the alcohols given below the corresponding esters were prepared:

-continued

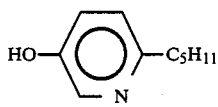

EXAMPLE 6

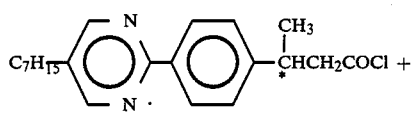

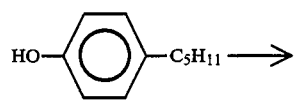

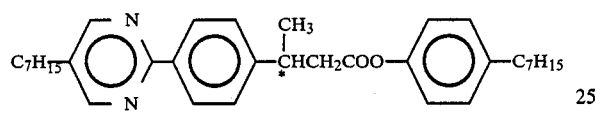

1.7 g of levorotatory 3-[4-(5-heptylpyrimidinyl-(2))-phenyl-(1)]-butyric acid ($a_D^{20} = -3.30$), obtained as in the previous example by resolution, are converted in the usual manner with SOCl₂ to the corresponding acid chloride, which is dissolved in 10 ml of diethylether and dropped to a solution containing 3 ml of pyridin and 1.64 g of 4-pentylphenol in 15 ml of diethylether at 0° C. After one hour additional stirring at 0° C., the mixture is stirred at room temperature overnight. After extraction of the neutral components and chromotographic separation optically active p-pentylphenyl 3-[4-(5-heptylpyrimidinyl-(2))-phenyl-(1)]-butyrate is obtained.

Analogously corresponding esters were prepared by esterification of the following alcohols:

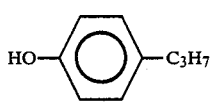

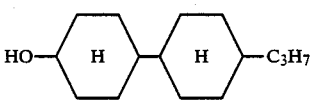

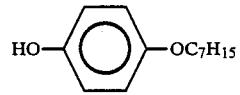

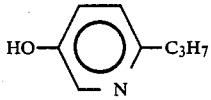

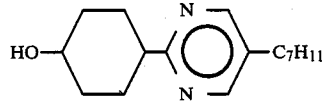

-continued

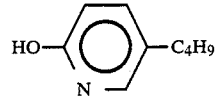

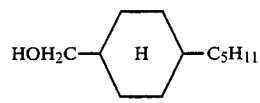

Example 7

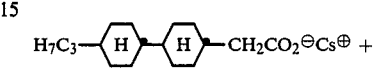

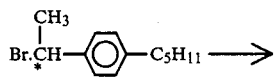

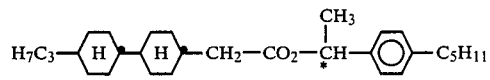

3.97 g of the Cs-salt derived from the all-trans 4-(4'-propylcyclohexyl)-cyclohexane-acetic acid, prepared from the equivalent amount of Cesium carbonate (Cs₂CO₃) and the acid by combining the components in dimethylformamide and evaporation of the dimethylformamide, are reacted with 2.55 g of dextrorotatory 1-bromo-1-(4-pentylphenyl)-ethane at 60° C. under stirring overnight in 30 ml dimethylformamide. The reaction mixture is poured into water, extracted with n-hexane, dried, evaporated and filtrated on silica-gel. After recrystallization from acetonitrile 1-(p-pentylphenyl)-1-ethyl all-trans-4-(4'-propylcyclohexyl)-cyclohexylacetate is obtained.

The following acids yield the corresponding esters by the same method:

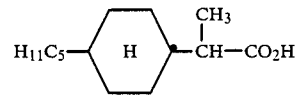

(levo- and dextrorotatory)

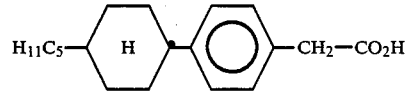

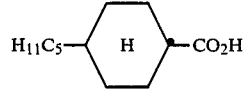

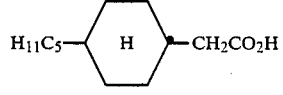

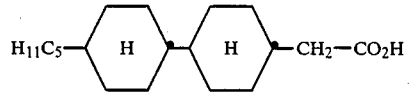

Example 8

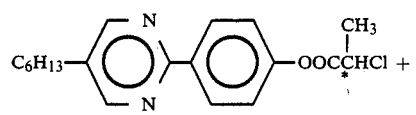
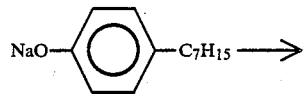
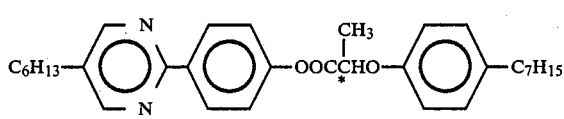

3.47 g (0.01 mole) of the optical active α-chloropropionicacidester of p-(5-hexylpyrimidin-2-yl)-phenol described in the German Patent Application DE-OS 3,515,373 are reacted with 2.15 g of sodium-p-heptylphenolate in 20 ml of N-methylpyrrolidone at 80° C. during two hours. The resulting reaction mixture is poured into water, extracted with toluene, the toluene layer is dried and evaporated. The residue is chromatographied on silica gel with toluene/1% acteone. The main fraction yields after recrystallization optically active p-(5-hexylpyrimidin-2-yl)-phenyl 2-(p-heptylphenoxy)propionate.

By reaction of the nucleophiles given below the corresponding derivatives were obtained in an analogous way.

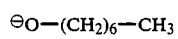
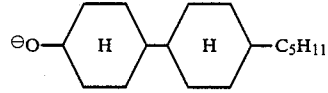
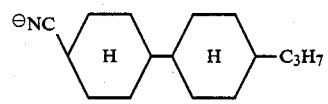
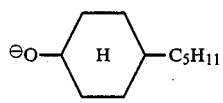
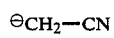
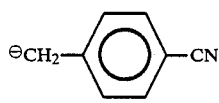
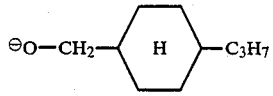

Example 9

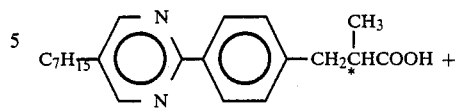
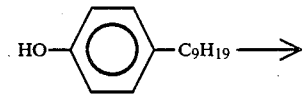
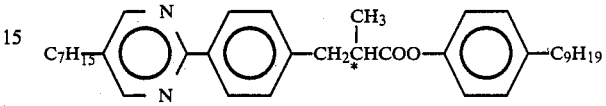

3.4 g (0.01 mol) of levorotatory 3-[4-(5-heptylpyrimidinyl-(2))-phenyl-(1)]-2-methylpropionic acid ($a_D^{20}=2.3°$ in $CH_2Cl_2$), obtained by resolution with (+)ephedrin and preparation of the racemic acid by hydrogenation of the corresponding α-methyl cinnamic acid with 5% Pd on charcoal in tetrahydrofuran, are esterified with 2.20 g of nonylphenol according to example 2. Optically active p-nonylphenyl 3-[4-(5-heptylpyrimidinyl-(2))-phenyl-(1)]-2-methylpropionate is obtained.

Analogously the following α-methylpropionic acid derivatives were converted to the corresponding 4-nonylphenolic esters.

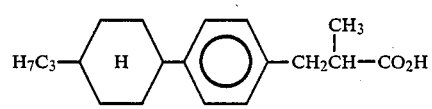
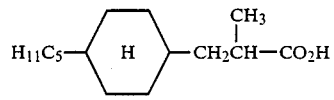
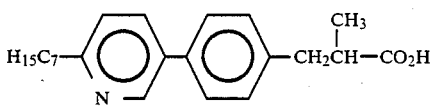
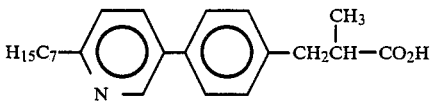
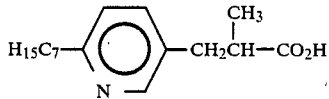
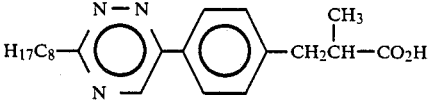
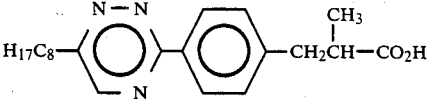

Example 10

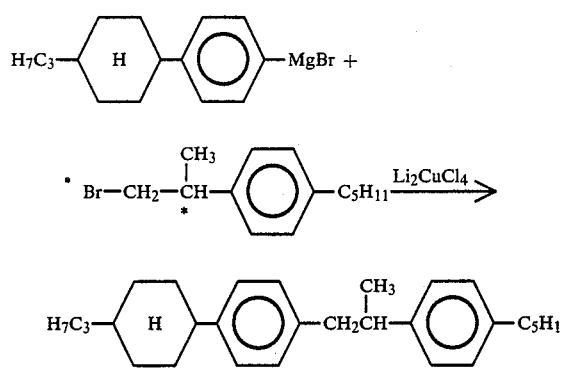

To a mixture of 2.7 g (0.01 mole) of levorotatory 4-(2-bromo-1-methylethyl-(1))-1-pentylbenzene and 66 mg of Li₂CuCl₄ (3 mol %) in 30 ml of tetrahydrofuran 10 ml of a tetrahydrofuran solution, containing the Grignard reagent prepared from 2.69 g (0.01 mole) of 1-bromo-4-(4-propylcyclohexyl)-benzene and 0.24 g of magnesium, are added dropwise under nitrogen and stirring at room temperature. After stirring for 16 hours at room temperature the reaction mixture is hydrolysed with 6N HCl and evaporated. The residue is treated with dilute HCl and diethylether. The etherical layer is washed until neutral, dried and evaporated. The residue yields after chromatography with n-hexane and crystallization the optically active cross coupled compound 1-[p-(trans-4-propylcyclohexyl)-phenyl]-2-(p-pentyl-phenyl)-propane.

Analogously the Grignard compounds of the following bromides were cross coupled.

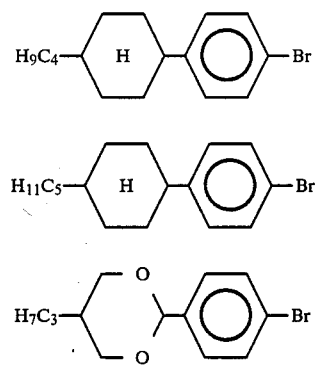

Example 11

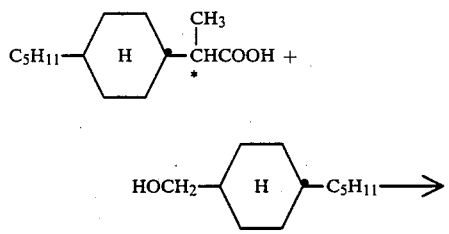

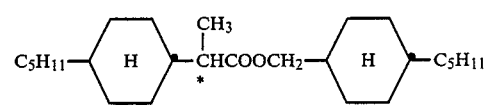

2.26 g (0.01 mole) levorotatory trans 2-(4-pentylcy-clohexyl-(1)-propionic acid, prepared by α-methylation of the corresponding acetic acid and separation of the diastereomers of the corresponding phenylglycinolamides and hydrolysis, are esterified as described in example 5 via the corresponding acid chlorid. Optically active trans-4-propyl-cyclohexylmethyl 2-(trans-4-pentylcyclohexyl-(1)-propionate is obtained.

By using the alcohols listed below the corresponding esters were obtained.

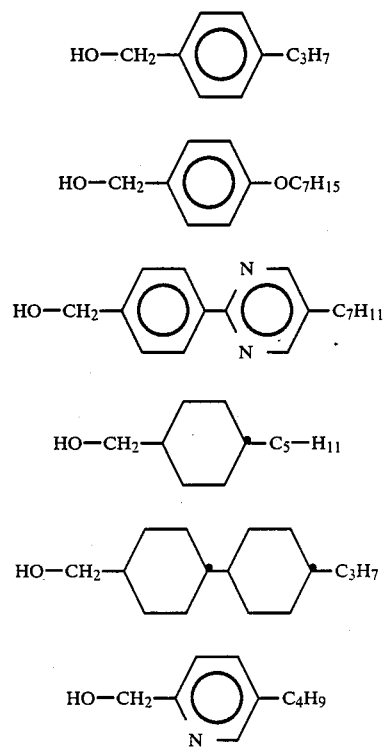

Example 12

7.9 ml azobisethoxycarbonyl are added dropwise to a solution of 10.9 g p-(trans-4-propyl-cyclohexyl)-phenol, 5.8 ml of (S)-ethyl lactate, and 3.1 g triphenylphosphine in 150 ml of tetrahydrofuran at room temperature.

The resulting mixture is stirred over night and evaporated. A suspension of the residue in a mixture of 90 ml of CH₃OH (90%) and 50 ml of CH₂Cl₂ is mixed with 5 ml of H₂O₂. After 15 minutes aqueous Na₂S₂O₅ and subsequently 100 ml of water are added. The organic layer is washed with NaHCO₃, water and dried over Na₂SO₄. After evaporation the residue is chromatographied on silica gel. Opticall active ethyl 2-[p-(trans-4-propylcyclohexyl(-phenoxy]-propanoate is obtained, bp. 180° (0.06 Torr).

In a similar way the following phenols yield the corresponding lactate ethers by etherification with ethyl lactate, methyl lactate, propyl lactate, hexyl lactate, heptyl lactate, 2-methylbutyl lactate or similar lactates:

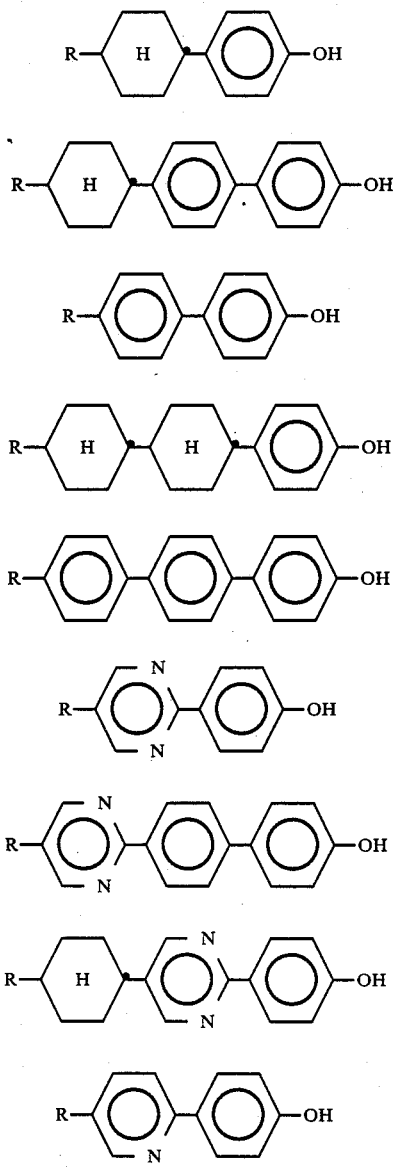

Example 13

To a mixture of 4-(4'-hydroxybiphenyl-4-yl)-1-cyan-1-octylcyclohexane (19.4 g), ethyl lactate (6.5 g) and triphenylphosphine (13.1 g) in tetrahydrofuran (300 ml) was added diethylazodicarboxylate (9.6 g) dissolved in tetrahydrofuran. The mixture was stirred for 1 hour at 50° C. and then left to stand overnight. The solvent was removed and the residue was dissolved in hot toluene (100 ml), which was then colled to 0° C. and filtered. The product was isolated from the filtrate by chromatography.

By this route optically active 2-(4'-(4-cyan-4-octylcyclohexyl)biphenyl-4-yloxy) propionic acid esters were obtained.

By analogous methods using alkyl lactates and phenols of formulae:

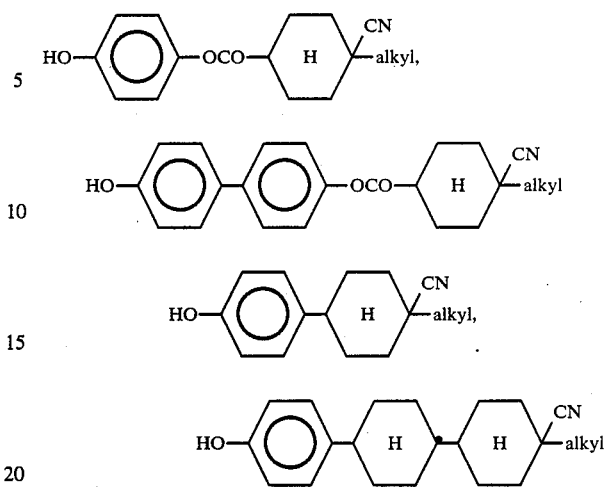

analogous compounds were prepared.

Example 14

To a mixture of p-hydroxybenzoic acid-(4-cyano-4-heptylcyclohexyl)-ester (20.6 g), prepared by reacting 4-cyano-4-cyclohexanol with p-benzyloxybenzoic acid and removing the benzyl group by catalytic hydrogenation, optically active hexyl lactate (11.5 g) and triphenylphosphine (15.7 g) in tetrahydrofuran (150 ml) was added a solution of diethylazodicarboxylate in tetrahydrofuran. The mixture was stirred for 1 hour at 50° C. and the solvent was removed after 12 hours standing. The residue was dissolved in hot toluene (100 ml), cooled, filtered and the product was isolated by chromatography and crystallisation.

By this route optically active p-(4-cyano-4-heptylcyclotexyloxycarbonyl)phenoxypropionic acid hexyl esters were obtained.

By analogous routes using alkyl lactates and the phenols below, analogous compounds were prepared.

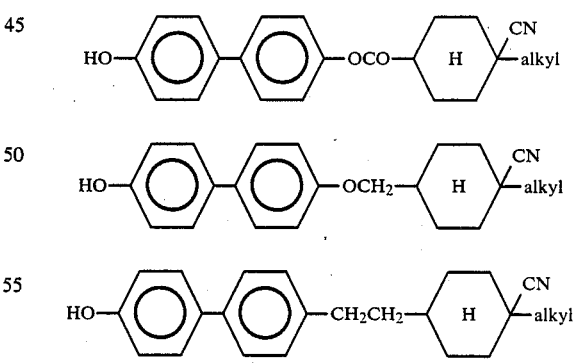

Example 15

Preparation of:

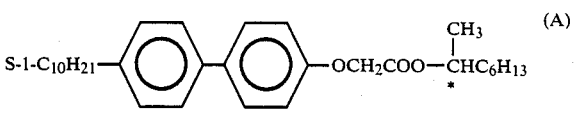

(S-1-methyl heptyl 4-n-decylbiphenyl-4'-oxyacetate)

Stage I (ethyl 4-n-decylbiphenyl-4'-oxyacetate)

A 500 ml round bottomed flask was charged with 4-n-decyl-4'-hydroxybiphenyl (10 g), ethylbromo acetate (6.5 g), anhydrous potassium carbonate (6.6 g), and butanone (160 mls). The resulting mixture was stirred and boiled under reflux for 20 hours. The reaction mixture was filtered hot through a Whatman 541 filter paper, and the butanone removed on a rotary evaporator to yield the crude product as a light yellow solid (12 g). The material was purified by recrystallization from 24 mls of industrial methylated spirit to yield a white crystalline product (8.9 g).

Stage II (4-n-decylbiphenyl-4'-oxyacetic acid)

A mixture of ethyl 4-n-decylbiphenyl-4'-oxyacetate (9.8 g), potassium hydroxide (3.5 g), water (11 mls), and industrial methylated spirit(400 mls) was stirred and heated under reflux overnight. The reaction mixture was cooled, added to 2 liters of cold water and acidified to pH 1 by the addition of concentrated hydrochloric acid. The resulting precipitated solid was filtered off, dried, and used in the following stage of the synthesis without further purification. The yield was 8.3 grams.

Stage III (S-1-methylheptyl 4-n-decylbiphenyl-4'-oxyacetate)

A mixture of 4-n-decylbiphenyl-4'-oxyacetic acid (4 g), S-2-octanol (1.56 g), dicyclohexyl carbodiimide (2.47 g), 4-dimethylamino pyridine (0.2 g) and dichloromethane (50 mls) was stirred overnight at room temperature. The reaction mixture was filtered, the solid residue washed with dichloromethane (25 mls) and the combined liquid extracts evaporated to dryness on a rotary evaporator. The product was an off white solid (5.2 g). The product was purified by chromatography on 52 g neutral alumina, eluted with petroleum ether, followed by recrystallisation from 10 mls of industrial methylated spirit. The yield of pure white product, purity 99.9% by hplc was 1.15 g. Melting point was recorded as 42°–42.5° C.

By analogous methods the following compounds were prepared:

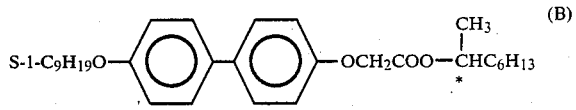

obtained as white solid, purity by hplc 99.5% mpt. 53.5°–54° C.

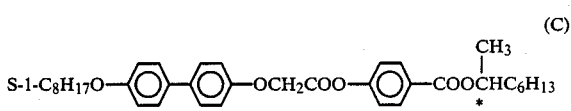

solid xtal $-S_C=87°$ C.; $S_C-N=110°$ C.; $N-I=111°$ C.

Ferroelectric smectic liquid crystal compositions were prepared containing compounds (A) and (B) above. Each composition contained 10 wt % of the compound in a host consisting of:

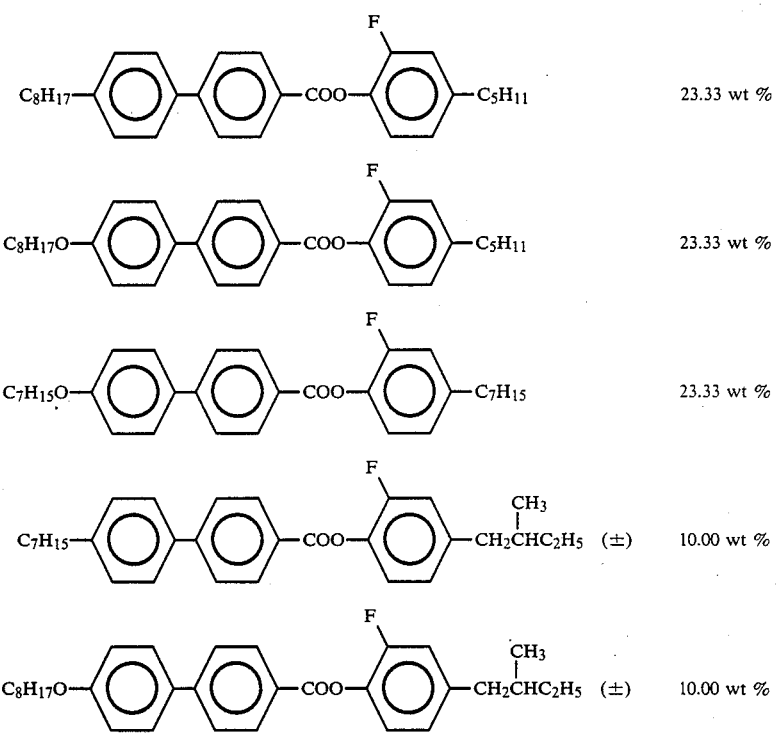

totalling 100 wt % with the compound (A) or (B). The mixtures are designated mixture (A) and (B) as appropriate below:

| Mixture→ | LC Transitions (°C.) | | Ps (nC cm$^{-2}$) | | |
|---|---|---|---|---|---|
| | (A) | (B) | Temp. (°C.) | (A) | (B) |
| $S_C$—$S_A$ | 71.3 | 80.1 | 20 | 8.9 | 11.3 |
| $S_A$—N* | 88.1 | 93.0 | 30 | 6.6 | 8.2 |
| N*—I | 127.4 | 130.9 | 40 | 5.5 | 6.6 |
| | | | 50 | 4.1 | 5.4 |
| | | | 60 | 2.7 | 4.2 |
| | | | 70 | 0.2 | 2.7 |

Example 16

From p-hexylbenzoic acid and 1-(4'-octoxybiphenyl-4-yl) propan-2-ol, prepared from S-(−)propylene oxide, was made the (+)-p-hexylbenzoic acid (1-)(4'-octoxybiphenyl-4-yl)-2-propyl ester:

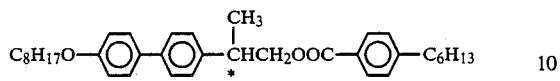

This had a melting point of 67° C. and $[\alpha]_D^{20}$ of +66.0° at a concentration of 5 wt % in dichloromethane.

Example 17

Properties of some other compounds of formula I which were prepared using the methods described herein are given below.

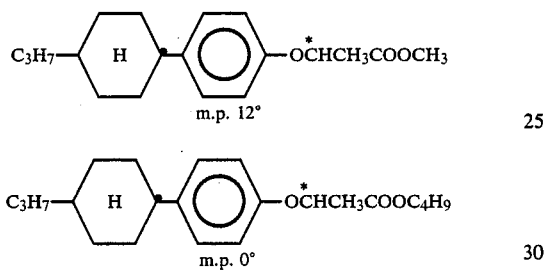

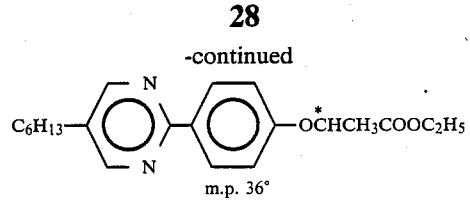

m.p. 36°

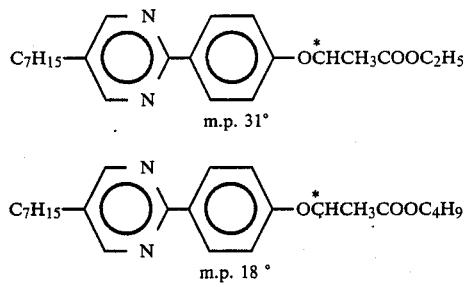

m.p. 31° m.p. 18°

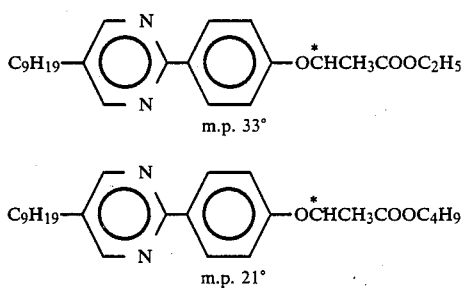

m.p. 33° m.p. 21°

| | mp (°C.) | $[\alpha]_{24}^D$ (CHCl$_3$) |
|---|---|---|
| (+)-C$_{C10}$H$_{21}$—⌬—⌬—OCHCOOC$_2$H$_5$ (CH$_3$) | 38 | +19.1 |
| (+)—⌬—CH$_2$O—⌬—OCHCOOC$_2$H$_5$ (CH$_3$) | (bp 178 0.01 mmHg) | +21.2 |
| (−)-C$_{C3}$H$_7$—⌬—⌬—OOCCHOC$_{10}$H$_{21}$ (CH$_3$) | 53 | −12.8 |

Example 18

An example of a ferroelectric smectic liquid crystal composition which includes a compound of Formula I.

| Component | wt % |
|---|---|
| 2-p-nonyloxyphenyl-5-heptylpyrimidine | 3 |
| 2-p-hexyloxyphenyl-5-nonylpyrimidine | 7 |
| 2-p-nonyloxyphenyl-5-nonylpyrimidine | 23 |
| r-1-cyano-cis-4-(4'-octyloxybiphenyl-4-yl)-1-butylcyclohexane | 28 |
| r-1-cyano-cis-4-(4'-heptylbiphenyl-4-yl)-1-hexylcyclohexane | 14 |
| r-1-cyano-cis-4-(trans-4-pentylcyclohexyl)-1-(trans-4-pentyl-cyclohexyl)-cyclohexane) | 6 |

-continued

| Component | wt % |
|---|---|
| 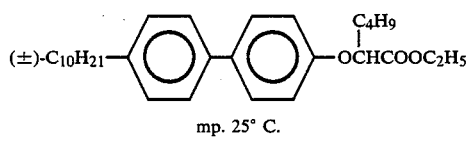 | 10 |
| 2-p-heptyloxyphenyl-5-heptylpyrimidine | 3 |
| 2-p-octyloxyphenyl-5-heptylpyrimidine | 3 |
| 2-p-hexyloxyphenyl-5-heptylpyrimidine | 3 |

The above mixture showed:
$S_C$ 54 $S_A$ 56 Ch 95 I
The spontaneous polarization Ps was +4.3 nCcm$^{-2}$ at 25° C.

Example 19

An example of a ferroelectric smectic liquid crystal composition:

| Component | wt. % |
|---|---|
| 2-p-nonyloxyphenyl-5-heptylpyrimidine | 3 |
| 2-p-hexyloxyphenyl-5-nonylpyrimidine | 7 |
| 2-p-nonyloxyphenyl-5-nonylpyrimidine | 23 |
| r-l-cyano-cis-4-(4'-octyloxybiphenyl-4-yl)-1-butylcyclohexane | 28 |
| r-l-cyano-cis-4-(4'-heptylbiphenyl-4-yl)-1-hexylcyclohexane | 14 |
| r-l-cyano-cis-4-(trans-4-pentylcyclohexyl-1-(trans-4-pentyl-cyclohexyl)-cyclohexane | 6 |
| 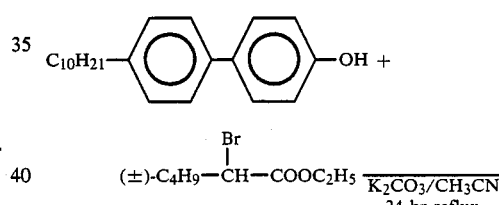 | 10 |
| 2-p-heptyloxyphenyl-5-heptylpyrimidine | 3 |
| 2-p-octyloxyphenyl-5-heptylpyrimidine | 3 |

The above mixture showed:
$S_C^*$ 63 $S_A$ 64 Ch 89 I
The spontaneous polarization Ps was +10.4 nCcm$^{-2}$ at 20° C.

Example 20

The racemic compound:

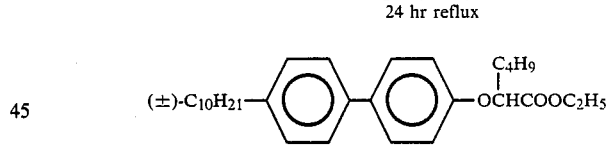

mp. 25° C.

was prepared using a modification of route A in which the ethyl ester of the known α-hydroxycarboxylic acid C$_4$H$_9$CH(OH)COOH was used instead of ethyl lactate, from which the sulphonate was prepared. By using other known α-hydroxycarboxylic acids, e.g.

| |
|---|
| C$_2$H$_5$CH(OH)COOH |
| C$_3$H$_7$CH(CH)COCH |
| C$_5$H$_{11}$ CH(OH)COOH | and preparing other alkyl, cycloalkyl or phenyl etc esters of such acids, analogous compounds could be prepared.

Alternately the α-hydroxycarboxylic acid could be synthesised from known aldehydes via the cyanohydrins, and subsequent hydrolysis i.e.:

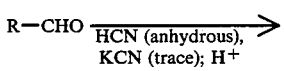

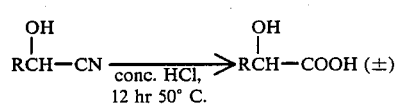

The racemic acid may be optically resolved using brucine, via known methods. R represents the appropriate alkyl group.

Alternately, the above compound was prepared by the reaction of commerically available (Aldrich) (±)-ethyl-2-bromo hexanoate with the appropriate phenol:

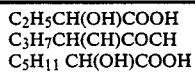

The product was isolated and purified using standard procedures.

An example of the use of a compound of Formula I in a liquid crystal material and device embodying the present invention will now be described with reference to FIG. 2.

Figure 2:
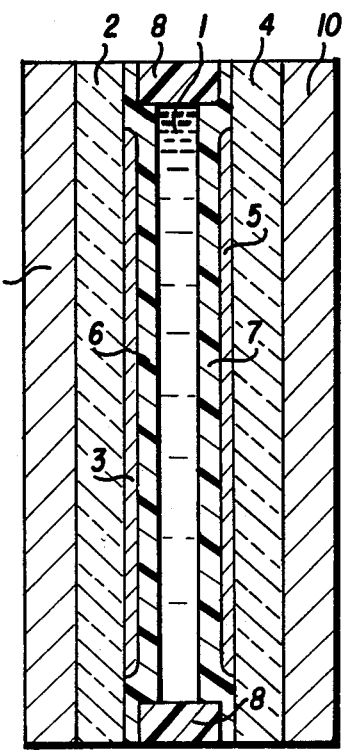
FIG. 2 which shows a cross section through a liquid crystal device.

In FIG. 2 a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2,4 bearing the layers 3,5 are respectively coated by films 6,7 of a polyimide polymer. Prior to construction of the cell the films 6 and 7 are rubbed with a soft tissue in a given direction the rubbing directions being arranged parallel upon construction of the cell. A spacer 8 e.g. of polymethylmethacrylate, separates the slides 2,4 to the required distance, e.g. 5 microns. The liquid crystal material 1 is introduced between the slides 2,4 to the required distance, e.g. 5 microns. The liquid crystal material 1 is introduced between the slides 2,4 by filling the space between the slides 2,4 and spacer 8 and sealing the spacer 8 in a vacuum in a known way. Preferably, the liquid crystal material in the smectic A or isotropic liquid phase (obtained by heating the material) when it is introduced beteen the slides 2,4 to facilitate alignment of the liquid crystal molecules with the rubbing directions on the slides 2,4.

A polarizer 9 is arranged with its polarization axis parallel to the rubbing direction on the films 6,7 and an analyzer (crossed polarizer)10 is arranged with its polarization axis perpendicular to that rubbing direction.

When a square wave voltage (from a conventional source not shown) varying between about +10 volts and −10 volts is applied across the cell by making contact with the layers 3 and 5 the cell is rapidly switched upon the change in sign of the voltage between a dark state and a light state as explained above.

In an alternative device (not shown) based on the cell construction shown in FIG. 2 the layers 3 and 5 may be selectively shaped in a known way, e.g. by photoetching or deposition through a mask, e.g. to provide one or more display symbols, e.g. letters, numerals, words or graphics and the like as conventionally seen on displays. The electrode portions formed thereby may be addressed in a variety of ways which include multiplexed operation.

The ferroelectric smectic liquid crystal compositions described above, which show room temperature $S_C$ phases may be used as the liquid crystal material 1.

The compositions of Examples 15, 18 and 19 were particularly suitable for use in this device.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A ferroelectric smectic liquid crystal material, being a mixture of compounds, wherein at least one of said compounds is a compound of formula:

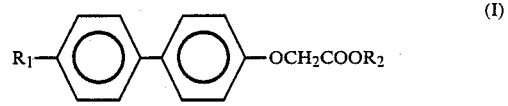

(I)

wherein $R_1$ is $C_1$–$C_{12}$ straight chain or branched alkyl or alkoxy, $R_2$ is $C_4$–$C_{12}$ chiral alkyl, and the phenyl rings may carry one lateral fluorine substituent, and at least one of said compounds is a compound which shows a smectic phase, the mixture having a composition:

compound(s) of formula I: 1–50 wt %
compound(s) showing a smectic phase: 50–99 wt %

2. A material according to claim 1 wherein $R_2$ is 1-methylheptyl.

3. A material according to claim 1 or 2 wherein $R_1$ is $C_3$–$C_{12}$ n-alkyl.

4. A material according to claim 1 wherein $R_2$ is optically active 1-methylheptyl and $R_1$ is selected from the group consisting of n-decyl and n-nonyloxy.

5. A material according to claim 1 wherein at least one of the compounds shows a smectic phase has a formula:

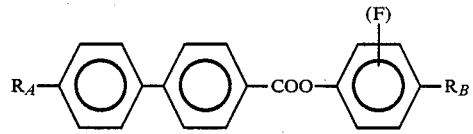

wherein $R_A$ and $R_B$ are independently $C_1$–$C_{12}$ alkyl or alkoxy.

6. A material according to claim 5 wherein $R_A$ is n-alkyl or n-alkoxy and the fluorine is at the ring position adjacent to the —COO—link.

7. A liquid crystal electro-optic display device comprising a liqiud crystal material as claimed in claim 1.

* * * * *